United States Patent
Mallo et al.

(10) Patent No.: US 10,052,275 B2
(45) Date of Patent: *Aug. 21, 2018

(54) SURFACTANT-FREE SELF-REVERSIBLE REVERSE LATEX, AND USE OF SAME AS A THICKENING AGENT IN A COSMETIC COMPOSITION

(71) Applicants: Paul Mallo, Croissy-sur-Seine (FR); Olivier Braun, St Just St Rambert (FR)

(72) Inventors: Paul Mallo, Croissy-sur-Seine (FR); Olivier Braun, St Just St Rambert (FR)

(73) Assignee: SOCIETE D'EXPLOITATION DE PRODUITS POUR LES INDUSTRIES CHIMIQUES SEPPIC, Paris (FR)

( * ) Notice: Subject to any disclaimer, the term of this patent is extended or adjusted under 35 U.S.C. 154(b) by 263 days.

This patent is subject to a terminal disclaimer.

(21) Appl. No.: 14/403,461

(22) PCT Filed: May 29, 2013

(86) PCT No.: PCT/FR2013/051205
§ 371 (c)(1),
(2) Date: Nov. 24, 2014

(87) PCT Pub. No.: WO2014/001668
PCT Pub. Date: Jan. 3, 2014

(65) Prior Publication Data
US 2015/0098915 A1   Apr. 9, 2015

(30) Foreign Application Priority Data

Jun. 25, 2012 (FR) ...................... 12 55994

(51) Int. Cl.
| | |
|---|---|
| A61K 8/81 | (2006.01) |
| A61Q 19/00 | (2006.01) |
| A61Q 15/00 | (2006.01) |
| A61Q 1/14 | (2006.01) |
| A61Q 5/00 | (2006.01) |
| A61Q 5/02 | (2006.01) |
| A61K 8/84 | (2006.01) |
| A61Q 17/04 | (2006.01) |
| C08F 2/32 | (2006.01) |
| A61K 8/58 | (2006.01) |
| A61K 8/72 | (2006.01) |
| A61K 8/92 | (2006.01) |
| C08F 220/18 | (2006.01) |
| A61Q 19/04 | (2006.01) |
| A61Q 19/06 | (2006.01) |

(52) U.S. Cl.
CPC ............ *A61K 8/8152* (2013.01); *A61K 8/585* (2013.01); *A61K 8/72* (2013.01); *A61K 8/8147* (2013.01); *A61K 8/84* (2013.01); *A61K 8/922* (2013.01); *A61Q 1/14* (2013.01); *A61Q 5/00* (2013.01); *A61Q 5/002* (2013.01); *A61Q 5/02* (2013.01); *A61Q 15/00* (2013.01); *A61Q 17/04* (2013.01); *A61Q 19/00* (2013.01); *A61Q 19/002* (2013.01); *A61Q 19/004* (2013.01); *A61Q 19/008* (2013.01); *C08F 2/32* (2013.01); *C08F 220/18* (2013.01); *A61Q 19/04* (2013.01); *A61Q 19/06* (2013.01)

(58) Field of Classification Search
None
See application file for complete search history.

(56) References Cited

U.S. PATENT DOCUMENTS

| | | |
|---|---|---|
| 2,798,053 A | 7/1957 | Harold |
| 5,368,850 A | 11/1994 | Cauwet et al. |
| 5,373,044 A | 12/1994 | Adams et al. |
| 5,458,881 A | 10/1995 | Berger et al. |
| 5,510,100 A | 4/1996 | Picard et al. |
| 5,549,681 A | 8/1996 | Segmuller et al. |
| 5,670,471 A | 9/1997 | Amalric et al. |
| 5,679,656 A | 10/1997 | Hansenne |
| 5,888,482 A | 3/1999 | Amalric et al. |
| 5,958,431 A | 9/1999 | Brancq et al. |
| 6,099,829 A | 8/2000 | Tiefensee et al. |
| 6,353,034 B1 | 3/2002 | Amalric et al. |
| 6,645,476 B1 | 11/2003 | Morschhauser et al. |
| 7,462,363 B2 * | 12/2008 | Braun ............ A61K 8/06 424/401 |

(Continued)

FOREIGN PATENT DOCUMENTS

| | | |
|---|---|---|
| CN | 1984955 | 6/2007 |
| DE | 1 95 23 596 A1 | 1/1997 |

(Continued)

OTHER PUBLICATIONS

English Language Translation of DE 19625810 A1.*

(Continued)

*Primary Examiner* — Bethany P Barham
*Assistant Examiner* — Dominic Lazaro
(74) *Attorney, Agent, or Firm* — Young & Thompson

(57) ABSTRACT

Disclosed is a self-reversible reverse latex including: a) 25-80% by mass of a cross-linked anionic polyelectrolyte (P), resulting from the polymerization, for 100 mole percent: i)—of a molar proportion ≥30% and ≤95% of monomeric units from at least one monomer including a free, partially- or totally-salified strong acid function; and ii)—of a molar proportion >0% and ≤5% of at least one monomer with diethylenic or polyethylenic cross-linking; b) 0.5-10% by mass of a terpolymer of stearyl methacrylate, pentacosaethoxylated behenyl methacrylate and N,N-dimethylacrylamide, resulting from the polymerization, for 100 mole percent: of 80-95 mole percent of stearyl methacrylate, of 2.5-10 mole percent of N,N-dimethylacrylamide, and of 2.5-10 mole percent of pentacosaethoxylated behenyl methacrylate, c) 5-40% by mass of at least one oil, and d) 0.1-40% by mass of water; method of preparing same and use thereof as a thickener.

20 Claims, No Drawings

(56) References Cited

U.S. PATENT DOCUMENTS

| | | | |
|---|---|---|---|
| 8,937,101 B2 * | 1/2015 | Braun | A61K 8/8152 514/772.6 |
| 9,180,085 B2 * | 11/2015 | Braun | A61K 8/33 |
| 2001/0029287 A1 | 10/2001 | Loffler et al. | |
| 2005/0118119 A1 | 6/2005 | Stoltz et al. | |
| 2007/0265386 A1 | 11/2007 | Mallo et al. | |
| 2010/0272661 A1 * | 10/2010 | Braun | A61K 8/06 424/59 |
| 2013/0079420 A1 * | 3/2013 | Braun | A61K 8/8152 514/772.6 |

FOREIGN PATENT DOCUMENTS

| | | |
|---|---|---|
| DE | 196 25 810 A1 | 1/1998 |
| EP | 0 049 766 A1 | 4/1982 |
| EP | 0 301 532 A2 | 2/1989 |
| EP | 0 576 188 A1 | 12/1993 |
| EP | 0 603 019 A1 | 6/1994 |
| EP | 0 629 396 A1 | 12/1994 |
| EP | 0 684 024 A2 | 11/1995 |
| EP | 0 715 845 A1 | 6/1996 |
| EP | 0 816 403 A2 | 1/1998 |
| EP | 0 917 869 A2 | 5/1999 |
| EP | 1 069 142 A1 | 1/2001 |
| EP | 1 116 733 A1 | 7/2001 |
| FR | 2 734 496 A1 | 11/1996 |
| FR | 2961513 | 6/2010 |
| FR | 2 961 513 A1 | 12/2011 |
| GB | 1 499 731 A | 4/1975 |
| WO | 92/06778 A1 | 4/1992 |
| WO | 09/221318 A | 12/1992 |
| WO | 93/07856 A1 | 4/1993 |
| WO | 93/07902 A1 | 4/1993 |
| WO | 93/08204 A1 | 4/1993 |
| WO | 93/21316 A1 | 10/1993 |
| WO | 94/27561 A1 | 12/1994 |
| WO | 95/04592 A1 | 2/1995 |
| WO | 95/13863 A1 | 5/1995 |
| WO | 96/37285 A1 | 11/1996 |
| WO | 9809611 A1 | 3/1998 |
| WO | 98/22207 A1 | 5/1998 |
| WO | 98/47610 A1 | 10/1998 |
| WO | 03/061768 A2 | 7/2003 |
| WO | 2008/087326 A2 | 7/2008 |
| WO | 2011030044 A1 | 3/2011 |
| WO | WO-2011161349 A1 * 12/2011 ........... A61K 8/8152 |

OTHER PUBLICATIONS

Chinese Office Action dated May 24, 2016, in corresponding Chinese Application No. 201380033745.1.

International Search Report, dated Jul. 12, 2013, from corresponding PCT application.

FR Search Report, dated Sep. 10, 2012, from corresponding FR application.

* cited by examiner

SURFACTANT-FREE SELF-REVERSIBLE REVERSE LATEX, AND USE OF SAME AS A THICKENING AGENT IN A COSMETIC COMPOSITION

The present patent application relates to self-reversible water-in-oil reverse lattices, to the process for preparing them and to their use as thickeners and/or emulsifiers for products for caring for the skin, the scalp and the hair or for the manufacture of cosmetic, dermopharmaceutical or pharmaceutical preparations.

The cosmetics industry and the pharmaceutical industry very regularly use synthetic thickening polymers to increase the viscosity of creams, emulsions and various topical solutions. The synthetic thickening polymers currently used in these fields are in two physical forms, the powder form and the liquid form for which the polymer is dispersed in an oil by means of surfactants and which is commonly referred to as a reverse latex.

Among the thickening polymers in powder form, the ones most widely known are polymers based on acrylic acid or copolymers based on acrylic acid and esters thereof. Examples that will be mentioned are the polymers sold under the names Carbopol™ and Pemulen™. They are described especially in the American patents U.S. Pat. No. 5,373,044 and U.S. Pat. No. 2,798,053 and in European patent EP 0 301 532.

In cosmetics, homopolymers or copolymers based on 2-acrylamido-2-methylpropanesulfonic acid are also and still used in powder form. These thickening polymers are sold under the name Aristoflex™ and described especially in European patents EP 0 816 403, EP 1 116 733 and EP 1 069 142. There is also the polymer sold under the name Sepimax Zen™, which is a copolymer that is disclosed in the international patent applications published under the numbers WO 2008/087326 and WO 2011/030044. These thickeners in powder form are obtained by precipitating polymerization; the monomer(s) are dissolved in an organic solvent such as benzene, ethyl acetate, cyclohexane or tert-butanol.

These thickeners have the advantage of consisting only of the polymer itself. They usually do not contain any surfactant molecule. However, they have the inherent drawbacks of powders: formation of dust, long dissolution times, difficult handling.

The cosmetics industry also extensively uses thickeners in the form of reverse lattices and especially those sold by the Applicant. Mention will be made, for example, of the thickeners Sepigel™ 305, Simulgel™ 600, Simulgel™ EG, Simulgel™ NS, Simulgel™ A, Sepiplus™ 400,™ 265 and Sepiplus™ S. These thickeners are obtained by reverse emulsion polymerization. They have the advantage of being easier to handle and disperse very rapidly in water. Furthermore, these products develop remarkably high thickening performance qualities; these performance qualities are probably the consequence of the process for preparing them, a dispersed-phase polymerization reaction, which leads to polymers of very high molecular weights. Nevertheless, these thickeners in reverse latex form contain an oil and above all several surfactants that may occasionally induce cutaneous intolerance reactions on particularly sensitive individuals. The presence of these surfactants does not, either, allow the use of the reverse lattices for thickening "surfactant free" formulas.

In point of fact, reverse lattices generally contain at least two surfactants:
 At least one surfactant of low HLB which makes it possible to prepare the water-in-oil emulsion and to ensure its stability during the polymerization reaction. Sorbitan esters are good examples thereof.
 At least one surfactant of high HLB which makes it possible to make the final reverse latex (result of the emulsion polymerization) self-reversible. This means that, during the introduction of the thickener into the aqueous phase, dispersion and swelling of the polymer chains in water are readily obtained. Polysorbates or polyethoxylated alcohols are good examples thereof.

Surfactant-free thickening reverse lattices of high HLB are disclosed in the European patent application published under the number EP 0 917 869. Nevertheless, this solution is very imperfect since the thickening latex remains stabilized by means of at least one surfactant of low HLB. Furthermore, in order to obtain good inversion of the reverse latex, it is necessary to add directly to the cosmetic formula a surfactant of high HLB such as polysorbate or polyethoxylated alcohols.

The British patent application published under the number GB 1 499 731 discloses the synthesis of stabilizing copolymers of stearyl methacrylate/methacrylic acid type and other copolymers of the same type. Reverse lattices comprising these copolymers are described in the European patent application published under the number EP 0 161 038. European patent application EP 0 049 766 discloses the use of other stabilizing copolymers. However, it is observed that the stabilizing copolymers are often combined with standard surfactants of low HLB and above all that a surfactant of high HLB, such as ethoxylated nonylphenol, is incorporated into the reverse latex to make it self-reversible.

The inventors have sought to develop novel surfactant-free reverse lattices that are stable and self-reversible.

According to a first aspect, the subject of the invention is a composition in the form of a self-reversible reverse latex comprising, per 100% of its mass:
 a)—From 25 mass % to 80 mass % of a crosslinked anionic polyelectrolyte (P), derived from the polymerization, per 100 mol %:
  i)—of a molar proportion of greater than or equal to 30% and less than or equal to 95% of monomer units derived from at least one monomer comprising a free or partially or totally salified strong acid function;
  ii)—optionally of a molar proportion of greater than or equal to 10% and less than or equal to 65% of monomer units derived from at least one neutral monomer;
  iii)—optionally of a molar proportion of greater than or equal to 5% and less than or equal to 65% of monomer units derived from at least one monomer comprising a free or partially or totally salified weak acid function;
 and
  iv)—of a molar proportion of greater than 0% and less than or equal to 5% of at least one diethylenic or polyethylenic crosslinking monomer;
 b)—From 0.5 mass % to 10 mass % of a terpolymer of stearyl methacrylate, of pentacosaethoxylated behenyl methacrylate and of N,N-dimethylacrylamide, derived from the polymerization, per 100 mol %, of:
  80 mol % to 95 mol % of stearyl methacrylate,
  2.5 mol % to 10 mol % of N,N-dimethylacrylamide and
  2.5 mol % to 10 mol % of pentacosaethoxylated behenyl methacrylate,
 c)—From 5 mass % to 40 mass % of at least one oil, and
 d)—From 0.1 mass % to 40 mass % of water.

A subject of the invention is thus the composition as defined above, characterized especially in that it does not comprise therein either any surfactants of oil-in-water type or any surfactants of oil-in-water type.

The term pentacosaethoxylated behenyl methacrylate denotes the compound of formula (I):

$$\underset{H_2C}{\overset{R2}{\diagup}}\overset{\displaystyle\diagdown}{\underset{O}{\diagup}}\overset{\displaystyle}{O}\text{---}\!\!\!\left[\text{---}\right]_{\!\!n}\!\!\!\overset{\displaystyle}{O}\text{---}R1 \qquad (I)$$

In which R1 represents the docosanyl radical, R2 represents the methyl radical and n is equal to 25.

In the composition that is the subject of the present invention, the oil phase consists either of a commercial mineral oil containing saturated hydrocarbons such as paraffins, isoparaffins or cycloparaffins having at room temperature a density of between 0.7 and 0.9 and a boiling point of greater than about 250° C., for instance Isopar™ M, MARCOL™ 52 or MARCOL™ 82, sold by Exxon Chemical, or of a plant oil such as squalane of plant origin, or of a synthetic oil such as hydrogenated polyisobutene or hydrogenated polydecene, or of fatty acid esters of glycerol, whether they are monoesters, diesters or triesters, or of a mixture of several of these oils. Marcol™ 52 is a commercial oil corresponding to the definition of liquid petroleum jellies in the French Codex. It is a white mineral oil in accordance with the FDA regulations 21 CFR 172.878 and CFR 178.3620 (a) and it is registered in the US pharmacopea, US XXIII (1995) and in the European pharmacopea (1993).

According to another particular aspect, in the polyelectrolyte P of the composition that is the subject of the present invention, the strong acid function of the monomers comprising the same is especially the sulfonic acid function. Said monomers are, for example, free or partially or totally salified styrenesulfonic acid or, more particularly, free or partially or totally salified 2-methyl-2-[(1-oxo-2-propenyl) amino]-1-propanesulfonic acid (also known as 2-acrylamido-2-methylpropanesulfonic acid).

According to another particular aspect, in the polyelectrolyte P included in the composition that is the subject of the present invention, the weak acid function of the monomers comprising the same is especially the free or partially salified carboxylic acid function. Said monomers are, for example, acrylic acid, methacrylic acid, itaconic acid, maleic acid, 3-methyl-3-[(1-oxo-2-propenyl)amino]butanoic acid or 6-carboxyethyl acrylate of formula:

CH$_2$=CH—C(=O)—O—CH$_2$—CH$_2$—C(=O)—OH, said carboxylic acids being free or partially salified. This acid is more particularly free or partially salified acrylic acid or methacrylic acid.

For the monomers bearing a strong acid function or a weak acid function, the term "salified" indicates that the salts are alkali metal salts such as the sodium or potassium salts, or salts of nitrogenous bases such as the ammonium salt.

According to another particular aspect, in the polyelectrolyte P of the composition that is the subject of the present invention, the neutral monomer is chosen from acrylamide, N-methylacrylamide, N,N-dimethylacrylamide, N,N-diethylacrylamide, N-isopropylacrylamide, (2-hydroxyethyl) acrylate, (2,3-dihydroxypropyl)acrylate, (2-hydroxyethyl) methacrylate, (2,3-dihydroxypropyl)methacrylate, N-vinyl pyrrolidone, N-[2-hydroxy-1,1-bis(hydroxymethyl)ethyl] propenamide, (2-hydroxyethyl)acrylate and N-(2-hydroxyethyl)acrylamide).

According to another particular aspect, the terpolymer of stearyl methacrylate, of pentacosaethoxylated behenyl methacrylate and of N,N-dimethylacrylamide present in the composition that is the subject of the present invention is chosen from the following terpolymers:

Terpolymer of stearyl methacrylate, of pentacosaethoxylated behenyl methacrylate and of N,N-dimethylacrylamide [(A)/(B)/(C) mol ratio=87/5/8];

Terpolymer of stearyl methacrylate, of pentacosaethoxylated behenyl methacrylate and of N,N-dimethylacrylamide [(A)/(B)/(C) mol ratio=80/5/15];

Terpolymer of stearyl methacrylate, of pentacosaethoxylated behenyl methacrylate and of N,N-dimethylacrylamide [(A)/(B)/(C) mol ratio=85/10/5];

Terpolymer of stearyl methacrylate, of pentacosaethoxylated behenyl methacrylate and of N,N-dimethylacrylamide [(A)/(B)/(C) mol ratio=80/10/10];

Terpolymer of stearyl methacrylate, of pentacosaethoxylated behenyl methacrylate and of N,N-dimethylacrylamide [(A)/(B)/(C) mol ratio=90/5/5] or Terpolymer of stearyl methacrylate, of pentacosaethoxylated behenyl methacrylate and of N,N-dimethylacrylamide [(A)/(B)/(C) mol ratio=95/2.5/2.5)].

All these terpolymers are described in the International patent application published under the number WO 2011/161349.

According to another particular aspect, in the composition that is the subject of the present invention, the mass ratio between the terpolymer of stearyl methacrylate, of pentacosaethoxylated behenyl methacrylate and of N,N-dimethylacrylamide and the anionic polyelectrolyte P is greater than or equal to 1/100 and less than or equal to 1/5. It is more particularly greater than or equal to 5/100 and less than or equal to 1/5.

A subject of the invention is more particularly a composition in the form of a self-reversible reverse latex comprising, per 100% of its mass:

a)—From 25 mass % to 50 mass % of a branched or crosslinked anionic polyelectrolyte (P), derived from the polymerization, per 100 mol %:
  i)—of a molar proportion of greater than or equal to 30% and less than or equal to 95% of monomer units derived from at least one monomer comprising a free or partially or totally salified strong acid function;
  ii)—of a molar proportion of greater than or equal to 10% and less than or equal to 65% of monomer units derived from at least one neutral monomer;
and
  iv)—of a molar proportion of greater than 0% and less than or equal to 5% of at least one diethylenic or polyethylenic crosslinking monomer;

b)—From 1 mass % to 5 mass % of a terpolymer of stearyl methacrylate, of pentacosaethoxylated behenyl methacrylate and of N,N-dimethylacrylamide, derived from the polymerization, per 100 mol %;
  of 80 mol % to 95 mol % of stearyl methacrylate,
  of 2.5 mol % to 10 mol % of N,N-dimethylacrylamide, and
  of 2.5 mol % to 10 mol % of pentacosaethoxylated behenyl methacrylate, c)—From 10 mass % to 30 mass % of at least one oil, and
d)—From 20 mass % to 40 mass % of water.

A subject of the invention is more particularly a composition in the form of a self-reversible reverse latex comprising, per 100% of its mass:

a)—From 50 mass % to 80 mass % of a branched or crosslinked anionic polyelectrolyte (P), derived from the polymerization, per 100 mol %:
    i)—of a molar proportion of greater than or equal to 30% and less than or equal to 95% of monomer units derived from at least one monomer comprising a free or partially or totally salified strong acid function;
    ii)—of a molar proportion of greater than or equal to 10% and less than or equal to 65% of monomer units derived from at least one neutral monomer;
and
    iv)—of a molar proportion of greater than 0% and less than or equal to 5% of at least one diethylenic or polyethylenic crosslinking monomer;

b)—From 1 mass % to 10 mass % of a terpolymer of stearyl methacrylate, of pentacosaethoxylated behenyl methacrylate and of N,N-dimethylacrylamide, derived from the polymerization, per 100 mol %:
    of 80 mol % to 95 mol % of stearyl methacrylate,
    of 2.5 mol % to 10 mol % of N,N-dimethylacrylamide, and
    of 2.5 mol % to 10 mol % of pentacosaethoxylated behenyl methacrylate, c)—From 10 mass % to 40 mass % of at least one oil, and
d)—Not more than 5 mass % of water.

The composition according to the invention may also contain various additives such as complexing agents, transfer agents or chain-limiting agents.

According to another aspect of the present invention, a subject thereof is a process for preparing the composition as defined previously, characterized in that:

a) an aqueous phase (A) containing the monomers and the optional hydrophilic additives is emulsified in an organic phase (O) containing said terpolymer of stearyl methacrylate, of pentacosaethoxylated behenyl methacrylate and of N,N-dimethylacrylamide, the oil or the mixture of oils, a mixture consisting of the oils intended to be present in the final composition and, if necessary, one or more volatile oils and also the optional hydrophobic additives, b) the polymerization reaction is initiated by introducing into the emulsion formed in a) a free-radical initiator, and the reaction is then left to proceed, and, if desired, c) the reaction medium derived from step b) is concentrated by distillation, until said volatile oil has been completely removed.

The volatile oils that are suitable for use in the process as defined above are, for example, light isoparaffins comprising from 8 to 13 carbon atoms, for instance those sold under the names Isopar™ G, Isopar™ L or Isopar™ H or Isopar™ J.

According to a preferred implementation of the process as defined previously, the polymerization reaction is initiated with a redox couple, such as the cumene hydroperoxide/sodium metabisulfite couple, at a temperature of less than or equal to 10° C., and then performed virtually adiabatically up to a temperature of greater than or equal to 40° C., more particularly greater than or equal to 50° C., i.e. by controlling the temperature progress.

A subject of the invention is also the use of the terpolymer of stearyl methacrylate, of pentacosaethoxylated behenyl methacrylate and of N,N-dimethylacrylamide, derived from the polymerization, per 100 mol %:
    of 80 mol % to 95 mol % of stearyl methacrylate,
    of 2.5 mol % to 10 mol % of N,N-dimethylacrylamide and
    of 2.5 mol % to 10 mol % of pentacosaethoxylated behenyl methacrylate,
as stabilizer for the water-in-oil emulsion comprising all of the constituents necessary for the preparation of the composition in the form of a self-reversible reverse latex as defined previously, in which water-in-oil emulsion the reverse emulsion polymerization reaction proceeds.

A subject of the invention is also a cosmetic, dermopharmaceutical or pharmaceutical topical composition, characterized in that it comprises, as thickener and/or emulsifier, an effective amount of the composition as defined previously.

A topical composition according to the invention, intended to be applied to the skin, the scalp, the hair or mucous membranes of man or animals, may consist of a topical emulsion comprising at least one aqueous phase and at least one oil phase, which is in the form of a water-in-oil, or oil-in-water, or water-in-oil-in-water, or oil-in-water-in-oil emulsion. More particularly, this topical emulsion may consist of a fluid emulsion, such as a milk or a fluid gel. The oil phase of the topical emulsion may consist of a mixture of one or more oils.

A topical composition according to the invention may be intended for a cosmetic use or may be used for preparing a medicament for treating skin, scalp and mucous membrane diseases. In the latter case, the topical composition then comprises an active principle which may consist, for example, of an antiinflammatory agent, a muscle relaxant, an antifungal agent or an antibacterial agent.

When the topical composition is used as a cosmetic composition intended to be applied to the skin, the scalp, the hair or mucous membranes, it may or may not comprise an active principle, for example a moisturizer, a tanning agent, a sunscreen, an antiwrinkle agent, a slimming agent, a free-radical scavenger, an antidandruff agent, an antiacne agent or an antifungal agent.

More particularly, as examples of active principles optionally present in the topical composition according to the invention, mention may be made of: vitamins and derivatives thereof, especially esters thereof, such as retinol (vitamin A) and esters thereof (for example retinyl palmitate), ascorbic acid (vitamin C) and esters thereof, sugar derivatives of ascorbic acid (for instance ascorbyl glucoside), tocopherol (vitamin E) and esters thereof (for instance tocopherol acetate), vitamins B3 or B10 (niacinamide and derivatives thereof); compounds which show lightening or depigmenting action on the skin, for instance Sepiwhite™ MSH, arbutin, kojic acid, hydroquinone, Vegewhite™, Gatuline™, Synerlight™, Biowhite™, Phytolight™, Dermalight™, Clariskin™, Melaslow™ Dermawhite™, Ethioline, Melarest™, Gigawhite™, Albatine™, Lumiskin™; compounds showing calmative action, such as Sepicalm™ S, allantoin and bisabolol; antiinflammatory agents; compounds showing moisturizing action, for instance urea, hydroxyureas, glycerol, polyglycerols, glycerol glucoside, diglycerol glucoside, polyglyceryl glucosides, erythrityl glucoside, xylityl glucoside, sorbityl glucoside, sorbitol, the composition sold under the name Aquaxyl™; polyphenol-rich plant extracts, for instance extracts of grape, extracts of pine, extracts of wine, extracts of olives; compounds showing slimming or lipolytic action, such as caffeine or derivatives thereof, Adiposlim™, Adipoless™; N-acyl proteins; N-acyl peptides, for instance Matrixil™; N-acylamino acids; partial hydrolysates of N-acyl proteins; amino acids; peptides; total protein hydrolysates; soybean extracts, for example Raffermine™, wheat extracts, for example Tensine™ or Gliadine™, plant extracts such as tannin-rich plant extracts, isoflavone-rich plant extracts or terpene-rich plant extracts, freshwater or seawater algal extracts; marine extracts in general such as corals; essential waxes; bacterial extracts; ceramides; phospholipids; compounds showing antimicrobial action or purifying action, for instance Lipacide™ C8G, Lipacide™ UG, Sepicontrol™ A5; Octopirox™ or Sensiva™ SC50; compounds with an energizing or stimulating property, such as Physiogenyl™, panthenol and derivatives thereof such as Sepicap™ MP; anti-aging active agents such as Sepilift™ DPHP, Lipacide™ PVB, Sepivinol™, Sepivital™, Manoliva™, Phyto-Age™, Timecode™; Survicode™; active agents for preventing light-induced aging; active agents for protecting the integrity of the dermo-epidermal junction; active agents that increase the synthesis of the components of the extracellular matrix, for instance collagen, elastins, glycosaminoglycans; active agents that act favorably on chemical cell communication, such as cytokines or physical cell communication such as integrins; active agents that create a "heating" sensation on the skin, such as activators of the skin capillary circulation (for instance nicotinic acid derivatives) or products that create a "freshness" sensation on the skin (for instance menthol and derivatives thereof); active agents that improve the capillary circulation of the skin, for example venotonic agents; draining active agents; decongesting active agents, for instance *Ginkgo biloba*, ivy, common horsechestnut, bamboo, ruscus, butcher's broom, *Centella asiatica*, fucus, rosemary or sage extracts; agents for tanning or browning skin, such as dihydroxyacetone, isatin, alloxan, ninhydrin, glyceraldehyde, mesotartaric aldehyde, glutaraldehyde or erythrulose.

The term "effective amount" means that the topical composition according to the invention comprises a sufficient amount of reverse latex according to the invention to bring about a change in its rheology. The topical composition according to the invention usually comprises between 0.1% and 10% by weight of said self-reversible reverse latex defined above. The pH of the topical composition is generally between 3 and 9.

The topical composition may also comprise compounds conventionally included in compositions of this type, for example thickeners and/or gelling agents, stabilizers, film-forming compounds, solvents and cosolvents, hydrotropic agents, plasticizers, opacifiers, nacreous agents, overfatting agents, sequestrants, chelating agents, antioxidants, conditioners, deodorants, fragrances, essential oils, preserving agents, dyes, emollients, particles that afford a visual effect or that are intended for encapsulating active agents, exfoliating particles, texturizers, optical brighteners, insect repellents, sunscreens, mineral fillers or pigments.

As examples of thickeners and/or gelling agents optionally present in the topical composition according to the invention, mention may be made of hydrocolloids of plant or biosynthetic origin, for example xanthan gum, karaya gum, carrageenates, alginates; galactomannans, for instance tara gum, guar gum, fenugreek gum, locust bean gum, cassia gum; silicates; cellulose and derivatives thereof; starch and hydrophilic derivatives thereof; polyurethanes.

As examples of deodorants optionally present in the topical composition according to the invention, mention may be made of alkali metal silicates, zinc salts such as zinc sulfate, zinc gluconate, zinc chloride, zinc lactate; quaternary ammonium salts such as cetyltrimethylammonium salts, cetylpyridinium salts; glycerol derivatives such as glycerol caprate, glycerol caprylate, polyglycerol caprate; 1,2-decanediol; 1,3-propanediol; salicylic acid; sodium bicarbonate; cyclodextrins; metal zeolites; Triclosan™, aluminum bromohydrate, aluminum chlorohydrates, aluminum chloride, aluminum sulfate, aluminum zirconium chlorohydrates, aluminum zirconium trichlorohydrate, aluminum zirconium tetrachlorohydrate, aluminum zirconium pentachlorohydrate, aluminum zirconium octachlorohydrate, aluminum sulfate, sodium aluminum lactate, complexes of aluminum chlorohydrate and glycol, such as the complex of aluminum chlorohydrate and of propylene glycol, the complex of aluminum dichlorohydrate and of propylene glycol, the complex of aluminum sesquichlorohydrate and of propylene glycol, the complex of aluminum chlorohydrate and of polyethylne glycol, the complex of aluminum dichlorohydrate and of polyethylne glycol, the complex of aluminum sesquichlorohydrate and of polyethylene glycol.

As examples of solvents and cosolvents optionally present in the topical composition according to the invention, mention may be made of water, organic solvents, for instance glycerol, diglycerol, glycerol oligomers, ethylene glycol, propylene glycol, butylene glycol, hexylene glycol, diethylene glycol, xylitol, erythritol, sorbitol, water-soluble alcohols such as ethanol, isopropanol or butanol, and mixtures of water and of said organic solvents.

As examples of sunscreens optionally present in the topical composition according to the invention, mention may be made of any of those featured in the cosmetic directive 76/768/EEC amended Annex VII.

Among the organic sunscreens optionally present in the topical composition according to the invention, mention may be made of the family of benzoic acid derivatives such as para-aminobenzoic acids (PABA), especially the monoglycerol esters of PABA, the ethyl esters of N,N-propoxy PABA, the ethyl esters of N,N-diethoxy PABA, the ethyl esters of N,N-dimethyl PABA, the methyl esters of N,N-dimethyl PABA, the butyl esters of N,N-dimethyl PABA; the family of anthranilic acid derivatives such as homomenthyl-N-acetyl anthranilate; the family of salicylic acid derivatives such as amyl salicylate, homomenthyl salicylate, ethylhexyl salicylate, phenyl salicylate, benzyl salicylate or p-isopropanolphenyl salicylate; the family of cinnamic acid derivatives such as ethylhexyl cinnamate, ethyl-4-isopropyl cinnamate, methyl-2,5-diisopropyl cinnamate, p-methoxypropyl cinnamate, p-methoxyisopropyl cinnamate, p-methoxyisoamyl cinnamate, p-methoxyoctyl cinnamate (p-methoxy-2-ethylhexyl cinnamate), p-methoxy-2-ethoxyethyl cinnamate, p-methoxycyclohexyl cinnamate, ethyl-α-cyano-β-phenyl cinnamate, 2-ethylhexyl-α-cyano-β-phenyl cinnamate, di-para-methoxymono-2-ethylhexanoyl glyceryl cinnamate; the family of benzophenone derivatives such as 2,4-dihydroxybenzophenone, 2,2'-dihydroxy-4-methoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenylbenzophenone-2-carboxylate, 2-hydroxy-4-n-octyloxybenzophenone, 4-hydroxy-3-carboxybenzophenone; 3-(4'-methylbenzylidene)-d,l-camphor, 3-(benzylidene)-d,l-camphor, camphor benzalkonium methosulfate; urocanic acid, ethyl urocanate; the family of sulfonic acid derivatives such as 2-phenyl-5-benzimidazolesulfonic acid and salts thereof; the family of triazine derivatives such as hydroxyphenyltriazine, ethylhexyloxyhydroxyphenyl-4-methoxyphenyltriazine, 2,4,6-trianillino(p-carbo-2'-ethylhexyl-1'-oxy)-1,3,5-triazine, the 4,4-((6-(((1,1-dimethylethyl)amino)carbonyl)phenyl) amino)-1,3,5-triazine-2,4-diyldiimino)bis-(2-ethylhexyl) ester of benzoic acid, 2-phenyl-5-methylbenzoxazole, 2,2'-hydroxy-5-methylphenylbenzotriazole, 2-(2'-hydroxy-5'-t-octylphenyl)benzotriazole, 2-(2'-hydroxy-5'-methylphenyl)

benzotriazole; dibenzazine; dianisoylmethane, 4-methoxy-4"-t-butylbenzoylmethane; 5-(3,3-dimethyl-2-norbornylidene)-3-pentan-2-one; the family of diphenylacrylate derivatives such as 2-ethylhexyl 2-cyano-3,3-diphenyl-2-propenoate, ethyl 2-cyano-3,3-diphenyl-2-propenoate; the family of polysiloxanes such as benzylidene siloxane malonate.

Among the inorganic sunscreens, also known as "mineral sunblocks", optionally present in the topical composition according to the invention, mention may be made of titanium oxides, zinc oxides, cerium oxide, zirconium oxide, yellow, red or black iron oxides, and chromium oxides. These mineral sunblocks may or may not be micronized, may or may not have undergone surface treatments and may optionally be in the form of aqueous or oily predispersions.

Among the essential oils optionally present in the topical composition according to the invention, mention may be made of essential oils rich in sesquiterpene and terpene carbides, for instance essential oils of terebenthine, of juniper or of lemon; alcohol-rich essential oils, for instance essential oils of coriander or of rose; essential oils rich in alcohols and esters, for instance essential oils of lavender or of mint; aldehyde-rich essential oils, for instance essential oils of cinnamon, of lemongrass or of eucalyptus; ketone-rich essential oils, for instance essential oils of sage or of camphor tree; phenol-rich essential oils, for instance essential oils of thyme or of clove; ether-rich essential oils, for instance essential oils of anise, of star anise or of fennel; peroxide-rich essential oils, for instance essential oils of lamb's quarters and of garlic; sulfurous essential oils, for instance essential oils of cruciferae and of liliacaea.

According to yet another aspect, the invention relates to the use of the composition in the form of a self-reversible reverse latex for thickening a cosmetic, dermopharmaceutic or pharmaceutical composition comprising at least one aqueous phase.

The composition according to the invention is an advantageous replacement for those sold under the names Sepigel™ 305, Sepigel™ 501, Simulgel™ EG, Simulgel™ NS or Simulgel™ 600 by the applicant, since it also has good compatibility with the other excipients used for the preparation of formulations such as milks, lotions, creams, soaps, baths, balms, shampoos or hair conditioners. It may also be used with said products Sepigel or Simulgel. It is especially compatible with the concentrates described and claimed in international publications WO 92/06778, WO 95/04592, WO 95/13863, WO 96/37285, WO 98/22207 and WO 98/47610 or in FR 2734 496, with the surfactants described in WO 93/08204. It is particularly compatible with Montanov™ 68, Montanov™ 82, Montanov™ 202, Montanov™ L, Montanov™ 14 or Montanov™ S. It may also be used in emulsions of the type described and claimed in EP 0 629 396 and in cosmetically or physiologically acceptable aqueous dispersions with an organopolysiloxane compound chosen, for example, from those described in WO 93/05762 or in WO 93/21316. It may also be used for forming aqueous gels at cosmetically or physiologically acceptable acidic pH, such as those described in WO 93/07856; it may also be used in combination with nonionic celluloses, for example for forming styling gels such as those described in EP 0 684 024, or alternatively in combination with fatty acid esters of sugars, for forming compositions for treating the hair or the skin such as those described in EP 0 603 019 or alternatively in the shampoos or hair conditioners as described and claimed in WO 92/21316 or, finally, in combination with an anionic homopolymer such as Carbopol™ for forming hair treatment products such as those described in DE 195 23 596 or in combination with other thickening polymers.

The composition according to the invention is also compatible with active principles such as, for example, self-tanning agents such as dihydroxyacetone (DHA) or antiacne agents; it may thus be introduced into self-tanning compositions such as those claimed in EP 0 715 845, EP 0 604 249, EP 0 576 188 or in WO 93/07902.

It is also compatible with N-acylamino acid derivatives, which allows its use in calmative compositions especially for sensitive skin, such as those described or claimed in WO 92/21318, WO 94/27561 or WO 98/09611, and which also allows its use in human skin-lightening compositions such as those described or claimed in WO 2003/061 768.

When the composition as defined previously is intended for treating the skin and/or the scalp and/or mucous membranes, it more particularly comprises a reverse latex of anionic polyelectrolyte that is the subject of the present invention. The reverse lattices that are the subject of the present invention may be used as thickeners for textile printing pastes. The examples that follow illustrate the present invention without, however, limiting it.

EXAMPLE A

Self-Reversible Reverse Latex of an NaATBS/HEA Copolymer Crosslinked with MBA

Aqueous Phase Preparation

The following are placed in a beaker, with stirring:

672.5 g of a commercial solution at 55% by mass of the sodium salt of 2-methyl-2-[(1-oxo-2-propenyl)amino]-1-propanesulfonic acid (NaATBS), 20.8 g of 2-hydroxyethyl acrylate (HEA), 0.152 g of methylenebis(acrylamide) (MBA), 0.45 g of a commercial solution at 40% by mass of sodium diethylenetriaminepentaacetate.

The pH is adjusted to 4 with 2-methyl-2-[(1-oxo-2-propenyl)amino]-1-propanesulfonic acid and the aqueous phase is then made up to 700 g with water.

Preparation of the Organic Phase

The following are mixed together by simple stirring in a beaker:

220 g of Isopar™ M (C13/C14 isoparaffin), 20 g of a solution of stearyl methacrylate/N,N-dimethylacrylamide/behenyl methacrylate ethoxylated with 25 mol as a 46% solution in Isopar M, 0.15 g of AIBN (azobis(isobutyronitrile)).

The aqueous phase is then poured into the oil phase with stirring and the mixture is emulsified, while maintaining the beaker in an ice bath, using an Ultra-Turrax turbomixer until a viscosity of about 4600 mPa·s is obtained (Brookfield RVT M4, V20). The emulsion is then placed in the polymerization reactor. Sparging with nitrogen is performed for about 45 minutes while cooling the reactor to about 8° C. 10 cm$^3$ of a solution containing 0.17% (mass/volume) of cumene hydroperoxide in Isopar™ M are then added, followed by an aqueous solution of sodium metabisulfite at 0.27% (mass/mass) in water at a rate of 0.5 cm$^3$/minute. The introduction is stopped at the end of the exothermicity. A stable self-reversible reverse latex, referred to hereinbelow as the self-reversible reverse latex (1), is obtained at the end of polymerization.

Evaluation of the Properties

Viscosity of the self-reversible reverse latex (Brookfield RVT, M3, 20 rpm): η=1.800 mPa·s Viscosity of the self-reversible reverse latex mixed to 2% by mass in water (Brookfield RVT, spindle 5; 5 rpm): η=158 000 mPa·s This viscosity is obtained without addition of a surfactant. Furthermore, the rate of inversion is about 2 minutes and thus similar to that obtained for standard reverse lattices.

EXAMPLE B

Concentrated Self-Reversible Reverse Latex of an NaATBS/HEA Copolymer Crosslinked with MBA Preparation of the Aqueous Phase The same aqueous phase as that of Example A, with the exception of the amount of methylenebis(acrylamide) which is reduced to 0.028 g, is prepared.

Preparation of the Organic Phase

The following are mixed together by simple stirring in a beaker:

100 g of Isopar™ H 200 g of C8-C10 triglyceride 25 g of a solution at 46% in Isopar™ M of stearyl methacrylate/N,N-dimethylacrylamide/behenyl methacrylate ethoxylated with 25 mol in solution 0.15 g of AIBN (azobis(isobutyronitrile)).

The aqueous phase is poured into the oil phase with stirring and the mixture is emulsified, while maintaining the beaker in an ice bath, using an Ultra-Turrax turbomixer until a viscosity value of about (3000 mPa·s) is obtained (Brookfield RVT M4, V20). The emulsion is then placed in the polymerization reactor. Sparging with nitrogen is performed for about 45 minutes while cooling the reactor to about 8° C. 10 cm³ of a solution at 0.17% (mass/volume) of cumene hydroperoxide in C8-C10 triglyceride are then added, followed by an aqueous solution of sodium metabisulfite at 0.27% (mass/mass) in water at a rate of 0.5 cm³/minute. The introduction is stopped at the end of the exothermicity. Next, one hour after the end of the polymerization, the reactor is placed under partial vacuum to a value of about 17×10³ Pa and the temperature is adjusted to 80° C. so as to remove the Isopar™ H and the water by evaporation. After cooling, a concentrated self-reversible reverse latex containing about 65% by mass of anionic polyelectrolyte, referred to hereinbelow as the self-reversible reverse latex (2), is obtained. This latex is stable with respect to sedimentation and reverses spontaneously in water.

Evaluation of the Properties

Viscosity of the self-reversible reverse latex (Brookfield RVT, M3, 20 rpm): η=3.800 mPa·s.

Viscosity of the self-reversible reverse latex at 2% in water (Brookfield RVT, M5; 5 rpm): η=63 600 mPa·s.

This viscosity is obtained without the addition of surfactant. Furthermore, the rate of inversion is about 4 minutes and thus similar to that obtained for concentrated reverse lattices.

Viscosity of the self-reversible reverse latex at 2% in water+0.1% sodium chloride (Brookfield RVT, spindle 5; 5 rpm):

η=31 000 mPa·s.

Examples of Cosmetic Formulations

Proportions Expressed as Mass Percentages

EXAMPLE 1

Care Cream

| Cyclomethicone: | 10% |
|---|---|
| Self-reversible reverse latex (2): | 0.8% |
| Montanov™ 68: | 4.5% |
| Preserving agent: | 0.65% |
| Lysine: | 0.025% |
| EDTA (disodium salt): | 0.05% |
| Xanthan gum: | 0.2% |
| Glycerol: | 3% |
| Water: | qs 100% |

EXAMPLE 2

Care Cream

| Cyclomethicone: | 10% |
|---|---|
| Self-reversible reverse latex (1): | 0.8% |
| Montanov™ 68: | 4.5% |
| Perfluoropolymethyl isopropyl ether: | 0.5% |
| Preserving agent: | 0.65% |
| Lysine: | 0.025% |
| EDTA (disodium salt): Pemulen™ TR: | 0.05% |
| Glycerol: | 3% |
| Water: | qs 100% |

EXAMPLE 3

Aftershave Balm

Formula

| A | Self-reversible reverse latex (1): | 1.5% |
|---|---|---|
|  | Water: | qs 100% |
| B | Micropearl™ M100: | 5.0% |
|  | Sepicide™ CI: | 0.50% |
|  | Fragrance: | 0.20% |
|  | 95° ethanol: | 10.0% |

Procedure

Add B to A.

EXAMPLE 4

Satin Emulsion for the Body

Formula

| A | Simulsol™ 165: | 5.0% |
|---|---|---|
|  | Lanol™ 1688: | 8.50% |
|  | Shea butter: | 2% |
|  | Liquid paraffin: | 6.5% |
|  | Lanol™ 14 M: | 3% |
|  | Lanol™ S: | 0.6% |
| B | Water: | 66.2% |
| C | Micropearl™ M 100: | 5% |
| D | Self-reversible reverse latex (1): | 3% |

-continued

| E | Sepicide ™ CI | 0.3% |
|---|---|---|
|   | Sepicide ™ HB: | 0.5% |
|   | Monteine ™ CA: | 1% |
|   | Fragrance: | 0.20% |
|   | Vitamin E acetate: | 0.20% |
|   | Sodium pyrrolidinonecarboxylate (moisturizer): | 1% |

Procedure

Add C to B, emulsify B in A at 70° C., then add D at 60° C. and then E at 30° C.

EXAMPLE 5

Body Milk

Formula

| A | Simulson ™ 165: | 5.0% |
|---|---|---|
|   | Lanol ™ 1688: | 12.0% |
|   | Lanol ™ 14 M: | 2.0% |
|   | Cetyl alcohol: | 0.3% |
|   | Schercemol ™ OP: | 3% |
| B | Water: | qs 100% |
| C | Self-reversible reverse latex (2): | 0.35% |
| D | Sepicide ™ CI: | 0.2% |
|   | Sepicide ™ HB: | 0.5% |
|   | Fragrance: | 0.20% |

Procedure

Emulsify B in A at 70° C., add C, then add D at 60° C. and then E at 30° C.

EXAMPLE 6

O/W Cream

Formula

| A | Simulsol ™ 165: | 5.0% |
|---|---|---|
|   | Lanol ™ 1688: | 20.0% |
|   | Lanol ™ P: | 1.0% |
| B | Water: | qs 100% |
| C | Self-reversible reverse latex (2): | 2.50% |
| D | Sepicide ™ CI: | 0.20% |
|   | Sepicide ™ HB: | 0.30% |

Procedure

Introduce B into A at about 75° C.; add C at about 60° C., then D at about 45° C.

EXAMPLE 7

Non-Greasy Antisun Gel

Formula

| A | Self-reversible reverse latex (1): | 3.00% |
|---|---|---|
|   | Water: | 30% |
| B | Sepicide ™ C: | 0.20% |
|   | Sepicide ™ HB: | 0.30% |
|   | Fragrance: | 0.10% |
| C | Dye: | qs |
|   | Water: | 30% |
| D | Micropearl ™ M 100: | 3.00% |
|   | Water: | qs 100% |
| E | Silicone oil: | 2.0% |
|   | Parsol ™ MCX: | 5.00% |

Procedure

Introduce B into A; add C, then D and then E.

EXAMPLE 8

Antisun Milk

Formula

| A | Sepiperl ™ N: | 3.0% |
|---|---|---|
|   | Sesame oil: | 5.0% |
|   | Parsol ™ MCX: | 5.0% |
|   | Carrageenan: | 0.10% |
| B | Water: | qs 100% |
| C | Self-reversible reverse latex (1): | 0.80% |
| D | Fragrance: | qs |
|   | Preserving agent: | qs |

Procedure

Emulsify B in A at 75° C., then add C at about 60° C., then D at about 30° C. and adjust the pH if necessary.

EXAMPLE 9

Massage Gel

Formula

| A | Self-reversible reverse latex (1): | 3.5% |
|---|---|---|
|   | Water: | 20.0% |
| B | Dye: | 2 drops/100 g |
|   | Water: | qs |
| C | Alcohol: | 10% |
|   | Menthol: | 0.10% |
| D | Silicone oil: | 5.0% |

Procedure

Add B to A; then add to the mixture C and then D.

EXAMPLE 10

Massage Care Gel

Formula

| A | Self-reversible reverse latex (2): | 3.00% |
|---|---|---|
|   | Water: | 30% |
| B | Sepicide ™ CI: | 0.20% |
|   | Sepicide ™ HB: | 0.30% |
|   | Fragrance: | 0.05% |
| C | Dye: | qs |
|   | Water: | qs 100% |
| D | Micropearl ™ SQL: | 5.0% |
|   | Lanol ™ 1688: | 2% |

Procedure

Prepare A; add B, then C and then D.

EXAMPLE 11

Radiant-Complexion Gel

Formula

| | | |
|---|---|---|
| A | Self-reversible reverse latex (1): | 4% |
| | Water: | 30% |
| B | Elastin HPM: | 5.0% |
| C | Micropearl ™ M 100: | 3% |
| | Water: | 5% |
| | Sepicide ™ CI: | 0.2% |
| | Sepicide ™ HB: | 0.3% |
| | Fragrance: | 0.06% |
| | Sodium pyrrolidinonecarboxylate at 50%: | 1% |
| | Water: | qs 100% |

Procedure
Prepare A; add B, then C and then D.

EXAMPLE 12

Body Milk

Formula

| | | |
|---|---|---|
| A | Sepiperl ™ N: | 3.0% |
| | Glyceryl triheptonate: | 10.0% |
| B | Water: | qs 100% |
| C | Self-reversible reverse latex (1): | 1.0% |
| D | Fragrance: | qs |
| | Preserving agent: | qs |

Procedure
Melt A at about 75° C. Emulsify B in A at 75° C. and then add C at about 60° C., and then D.

EXAMPLE 13

Makeup-Removing Emulsion with Sweet Almond Oil

Formula

| | |
|---|---|
| Montanov ™ 68: | 5% |
| Sweet almond oil: | 5% |
| Water: | qs 100% |
| Self-reversible reverse latex (2): | 0.3% |
| Glycerol: | 5% |
| Preserving agent: | 0.2% |
| Fragrance: | 0.3% |

EXAMPLE 14

Moisturizing Cream for Greasy Skin

Formula

| | |
|---|---|
| Montanov ™ 68: | 5% |
| Cetylstearyl octanoate: | 8% |
| Octyle palmitate: | 2% |
| Water: | qs 100% |
| Self-reversible reverse latex (1): | 0.6% |
| Micropearl ™ M 100: | 3.0% |
| Mucopolysaccharides: | 5% |
| Sepicide ™ HB: | 0.8% |
| Fragrance: | 0.3% |

EXAMPLE 15

Alcohol-Free Calmative Aftershave Balm

Formula

| | |
|---|---|
| Mixture of N-lauryl amino acids: | 0.1% to 5% |
| Magnesium potassium aspartate: | 0.002% to 0.5% |
| Lanol ™ 99: | 2% |
| Sweet almond oil: | 0.5% |
| Water: | qs 100% |
| Self-reversible reverse latex (2): | 3% |
| Sepicide ™ HB: | 0.3% |
| Sepicide ™ CI: | 0.2% |
| Fragrance: | 0.4% |

EXAMPLE 16

Cream with AHA for Sensitive Skin

Formula

| | |
|---|---|
| Mixture of N-lauryl amino acids: | 0.1% to 5% |
| Magnesium potassium aspartate: | 0.002% to 0.5% |
| Lanol ™ 99: | 2% |
| Montanov ™ 68: | 5.0% |
| Water: | qs 100% |
| Self-reversible reverse latex (1): | 1.50% |
| Gluconic acid: | 1.50% |
| Triethanolamine: | 0.9% |
| Sepicide ™ NB: | 0.3% |
| Sepicide ™ CI: | 0.2% |
| Fragrance: | 0.4% |

EXAMPLE 17

Aftersun Calmative Care

Formula

| | |
|---|---|
| Mixture of N-lauryl amino acids: | 0.1% to 5% |
| Magnesium potassium aspartate: | 0.002% to 0.5% |
| Lanol ™ 99: | 10.0% |
| Water: | qs 100% |
| Self-reversible reverse latex (1): | 2.50% |
| Sepicide ™ HB: | 0.3% |
| Sepicide ™ CI: | 0.2% |
| Fragrance: | 0.4% |
| Dye: | 0.03% |

EXAMPLE 18

Makeup-Removing Milk

Formula

| | |
|---|---|
| Sepiperl ™ N: | 3% |
| Primol ™ 352: | 8.0% |
| Sweet almond oil: | 2% |
| Water: | qs 100% |
| Self-reversible reverse latex (1): | 0.8% |
| Preserving agent: | 0.2% |

EXAMPLE 19

Body Milk

Formula

| | |
|---|---|
| Sepiperl ™ N: | 3.5% |
| Lanol ™ 37T: | 8.0% |
| Solagum ™ L: | 0.05% |
| Water: | qs 100% |
| Benzophenone: | 2.0% |
| Dimethicone 350 cPs: | 0.05% |
| Self-reversible reverse latex (1): | 0.8% |
| Preserving agent: | 0.2% |
| Fragrance: | 0.4% |

EXAMPLE 20

Fluid Emulsion at Alkaline pH

| | |
|---|---|
| Marcol ™ 82: | 5.0% |
| NaOH: | 10.0% |
| Water: | qs 100% |
| Self-reversible reverse latex (2): | 1.5% |
| Lanol ™ 84D: | 8.0% |
| Lanol ™ 99: | 5.0% |
| Water: | qs 100% |

EXAMPLE 21

Antisun Milk

Formula

| | |
|---|---|
| Sepiperl ™ N: | 3.5% |
| Lanol ™ 37T: | 10.0% |
| Parsol ™ NOX: | 5.0% |
| Eusolex ™ 4360: | 2.0% |
| Water: | qs 100% |
| Self-reversible reverse latex (1): | 1.8% |
| Preserving agent: | 0.2% |
| Fragrance: | 0.4% |

EXAMPLE 22

Gel for the Contour of the Eyes

Formula

| | |
|---|---|
| Self-reversible reverse latex (1): | 2.0% |
| Fragrance: | 0.06% |
| Sodium pyrrolidinonecarboxylate: | 0.2% |
| Dow Corning ™ 245 Fluid: | 2.0% |
| Water: | qs 100% |

EXAMPLE 23

Leave-in Care Composition

Formula

| | |
|---|---|
| Self-reversible reverse latex (2): | 1.5% |
| Fragrance: | qs |
| Preserving agent: | qs |
| Dow Corning ™ X2 8360: | 5.0% |
| Dow Corning ™ Q2 1401: | 15.0% |
| Water: | qs 100% |

EXAMPLE 24

Slimming Gel

| | |
|---|---|
| Self-reversible reverse latex (1): | 5% |
| Ethanol: | 30% |
| Menthol: | 0.1% |
| Caffeine: | 2.5% |
| Extract of *ruscus*: | 2% |
| Extract of ivy: | 2% |
| Sepicide ™ HB: | 1% |
| Water: | qs 100% |

EXAMPLE 25

Alcohol-Free Calmative Aftershave Balm

Formula

| | | |
|---|---|---|
| A | Lipacide ™ PVB: | 1.0% |
| | Lanol ™ 99: | 2.0% |
| | Sweet almond oil: | 0.5% |
| B | Self-reversible reverse latex (1): | 3.5% |
| C | Water: | qs 100% |
| D | Fragrance: | 0.4% |
| | Sepicide ™ HB: | 0.4% |
| | Sepicide ™ CI: | 0.2% |

EXAMPLE 26

Refreshing Aftershave Gel

Formula

| | | |
|---|---|---|
| | Lipacide ™ PVB: | 0.5% |
| | Lanol ™ 99: | 5.0% |
| | Self-reversible reverse latex (2): | 2.5% |
| B | Water: | qs 100% |
| C | Micropearl ™ LM: | 0.5% |
| | Fragrance: | 0.2% |
| | Sepicide ™ HB: | 0.3% |
| | Sepicide ™ CI: | 0.2% |

EXAMPLE 27

Care for Greasy Skin

Formula

| A | Micropearl ™ M310: | 1.0% |
|---|---|---|
|   | Self-reversible reverse latex (1): | 5.0% |
|   | Octyl isononanoate: | 4.0% |
| B | Water: qs | 100% |
| C | Sepicontrol ™ A5: | 4.0% |
|   | Fragrance: | 0.1% |
|   | Sepicide ™ HB: | 0.3% |
|   | Sepicide ™ CI: | 0.2% |
| D | Capigel ™ 98: | 0.5% |
|   | Water: | 10% |

EXAMPLE 28

Cream with AHAs

Formula

| A | Montanov ™ 68: | 5.0% |
|---|---|---|
|   | Lipacide ™ PVB: | 1.05% |
|   | Lanol ™ 99: | 10.0% |
| B | Water: | qs 100% |
|   | Gluconic acid: | 1.5% |
|   | Triethanolamine: | 0.9% |
| C | Self-reversible reverse latex (1): | 1.5% |
| D | Fragrance: | 0.4% |
|   | Sepicide ™ HB: | 0.2% |
|   | Sepicide ™ CI: | 0.4% |

EXAMPLE 29

Non-Greasy Self-Tanning Product for the Face and Body

Formula

| A | Lanol ™ 2681: | 3.0% |
|---|---|---|
|   | Self-reversible reverse latex (1) | 2.5% |
| B | Water: | qs 100% |
|   | Dihydroxyacetone: | 3.0% |
| C | Fragrance: | 0.2% |
|   | Sepicide ™ HB: | 0.8% |
|   | Sodium hydroxide: | qs pH = 5 |

EXAMPLE 30

Antisun Milk with Monoi Oil

Formula

| A | Monoi oil: | 10% |
|---|---|---|
|   | Lipacide ™ PVB: | 0.5% |
|   | Self-reversible reverse latex (2): | 2.2% |
| B | Water: | qs 100% |
| C | Fragrance: | 0.1% |
|   | Sepicide ™ HB: | 0.3% |
|   | Sepicide ™ CI: | 0.1% |
|   | Octyl methoxycinnamate: | 4.0% |

EXAMPLE 31

Antisun Care for the Face

Formula

| A | Cyclomethicone and dimethiconol: | 4.0% |
|---|---|---|
|   | Self-reversible reverse latex (1): | 3.5% |
| B | Water: | qs 100% |
| C | Fragrance: | 0.1% |
|   | Sepicide ™ HB: | 0.3% |
|   | Sepicide ™ CI: | 0.21% |
|   | Octyl methoxycinnamate: | 5.0% |
|   | Titanium mica: | 2.0% |
|   | Lactic acid: | qs pH 6.5 |

EXAMPLE 32

Self-Tanning Emulsion

Formula

| A | Lanol ™ 99: | 15% |
|---|---|---|
|   | Montanov ™ 68: | 5.0% |
|   | Octyl para-methoxycinnamate: | 3.0% |
| B | Water: | qs 100% |
|   | Dihydroxyacetone: | 5.0% |
|   | Monosodium phosphate: | 0.2% |
| C | Self-reversible reverse latex (2): | 0.5% |
| D | Fragrance: | 0.3% |
|   | Sepicide ™ HB: | 0.8% |
|   | Sodium hydroxide: | qs pH 7.5. |

EXAMPLE 33

Gloss Gel

| Self-reversible reverse latex (1): | 1.5% |
|---|---|
| Volatile silicone: | 25% |
| Monopropylene glycol: | 25% |
| Demineralized water: | 10% |
| Glycerol: | qs. 100% |

EXAMPLE 34

Slimming Gel

| Self-reversible reverse latex (2): | 1.5% |
|---|---|
| Isononyl isononanoate: | 2% |
| Caffeine: | 5% |
| Ethanol: | 40% |
| Micropearl ™ LM: | 2% |
| Demineralized water: | qs. 100% |
| Preserving agent, fragrance: | qs |

EXAMPLE 35

Makeup-Removing Milk

| Simulsol ™ 165: | 4% |
|---|---|
| Montanov ™ 202: | 1% |

-continued

| | |
|---|---|
| Triglyceride caprylate-caprate: | 15% |
| Pecosil ™ DCT: | 1% |
| Demineralized water: | qs. 100% |
| Capigel ™ 98: | 0.5% |
| Self-reversible reverse latex (1): | 1% |
| Proteol ™ OAT: | 2% |
| Sodium hydroxide: | qs pH = 7 |

EXAMPLE 40

Restructuring "Rinse-Off" Cream Mask for Stressed and Embrittled Hair

Formula

| | |
|---|---|
| Ketrol ™ T: | 0.5% |
| Pecosil ™ SPP50: | 0.75% |
| N-cocoyl amino acids: | 0.70% |
| Butylene glycol: | 3.0% |
| Self-reversible reverse latex (1): | 3.0% |
| Montanov ™ 82: | 3.0% |
| Jojoba oil: | 1.0% |
| Lanol ™ P: | 6.0% |
| Amonyl ™ DM: | 1.0% |
| Lanol ™ 99: | 5.0% |
| Sepicide ™ HB: | 0.3% |
| Sepicide ™ CI: | 0.2% |
| Fragrance: | 0.2% |
| Water: qs | 100% |

EXAMPLE 36

Antisun Cream

| | |
|---|---|
| Simulsol ™ 165: | 3% |
| Montanov ™ 202: | 2% |
| Benzoate C12-C15: | 8% |
| Pecosil ™ PS 100: | 2% |
| Dimethicone: | 2% |
| Cyclomethicone: | 5% |
| Octyl para-methoxycinnamate: | 6% |
| Benzophenone-3: | 4% |
| Titanium oxide: | 8% |
| Xanthan gum: | 0.2% |
| Butylene glycol: | 5% |
| Demineralized water: | qs. 100% |
| Self-reversible reverse latex (2): | 1.5% |
| Preserving agent, fragrance: | qs |

EXAMPLE 37

Gel for Caring for Combination Skin

| | |
|---|---|
| Self-reversible reverse latex (1): | 4% |
| Plant squalane: | 5% |
| Dimethicone: | 1.5% |
| Sepicontrol ™ A5: | 4% |
| Xanthan gum: | 0.3% |
| Water: | qs. 100% |
| Preserving agent, fragrance: | qs. |

EXAMPLE 38

Haircare Lotion

Formula

| | |
|---|---|
| Butylene glycol: | 3.0% |
| Self-reversible reverse latex (1): | 3% |
| Simulsol ™ 1293: | 3.0% |
| Lactic acid: | qs. pH = 6 |
| Sepicide ™ HB: | 0.2% |
| Sepicide ™ C1: | 0.3% |
| Fragrance: | 0.3% |
| Water: | qs. 100% |

EXAMPLE 39

Protective and Relaxing Shampoo

Formula

| | |
|---|---|
| Amonyl ™ 675 SB: | 5.0% |
| Sodium lauryl ether sulfate at 28%: | 35.0% |
| Self-reversible reverse latex (2): | 3.0% |
| Sepicide ™ HB: | 0.5% |
| Sepicide ™ CI: | 0.3% |
| Sodium hydroxide: | qs pH = 7.2 |
| Fragrance: | 0.3% |
| Dye (FDC blue 1/yellow 5): | qs |
| Water: qs 100% | |

EXAMPLE 40

"Leave-on" Protective Product; Anti-Stress Care Formula for the Hair

Formula

| | |
|---|---|
| Ketrol ™ T: | 0.5% |
| Mixture of cocoyl amino acids: | 3.0% |
| Butylene glycol: | 5.0% |
| DC 1501: | 5.0% |
| Self-reversible reverse latex (2): | 4.0% |
| Sepicide ™ HB: | 0.5% |
| Sepicide ™ CI: | 0.3% |
| Fragrance: | 0.3% |
| Water: | qs 100% |

EXAMPLE 41

Fragrancing Emulsion

Formula

| | |
|---|---|
| Isononyl isononanoate: | 6% |
| Ethylhexyl glycerol: | 1% |
| Easynov ™ : | 2.5% |
| Self-reversible reverse latex (2): | 3% |
| Aquaxyl ™: | 3% |
| Water: | qs 100% |
| Ethanol: | 40% |
| Fragrance: | 2.0% |

EXAMPLE 42

Deodorant Emulsion

Formula

| Isononyl isononanoate: | 6% |
|---|---|
| Fragrance: | 0.1% |
| Phenoxyethanol & ethylhexyl glycerol: | 1% |
| Easynov ™: | 1.5% |
| Self-reversible reverse latex (2): | 2.5% |
| Lipacide ™UG: | 1% |
| Water: | qs 100% |

EXAMPLE 43

Antiperspirant Emulsion

Formula

| Isononyl isononanoate: | 6% |
|---|---|
| Ethylhexyl glycerol: | 1% |
| Easynov ™: | 2.5% |
| Self-reversible reverse latex (2): | 0.5% |
| Aquaxyl ™: | 3% |
| Water: | qs 100% |
| Aluminum chlorohydrate (50%): | 30% |

The definitions of the commercial products used in the examples are as follows:

Simulsol™ 1293 is hydrogenated and polyethoxylated castor oil, with an ethoxylation index equal to 40, sold by the company SEPPIC.

Capigel™ 98 is a liquid thickener based on acrylate copolymer sold by the company SEPPIC.

Ketrol™ T is xanthan gum sold by the company Kelco.

Lanol™ 99 is isononyl isononanoate sold by the company SEPPIC.

DC1501 is a mixture of cyclopentasiloxane and dimethiconol sold by the company Dow Chemical.

Montanov™ 82 is an emulsifier based on cetearyl alcohol and cocoylglucoside.

Montanov™ 68 (cetearyl glucoside) is a self-emulsifying composition as described in WO 92/06778, sold by the company SEPPIC.

Micropearl™ M 100 is an ultrafine powder with a very soft feel and a matting action, sold by the company Matsumo.

Sepicide™ CI, imidazolidine urea, is a preserving agent sold by the company SEPPIC.

Pemulen™ TR is an acrylic polymer sold by Goodrich.

Simulsol™ 165 is self-emulsifying glyceryl stearate sold by the company SEPPIC.

Lanol™ 1688 is an emollient ester with a nongreasy effect sold by the company SEPPIC.

Lanol™ 14 M and Lanol S are consistency factors sold by the company SEPPIC.

Sepicide™ HB, which is a mixture of phenoxyethanol, methylparaben, ethylparaben, propylparaben and butylparaben, is a preserving agent sold by the company SEPPIC.

Monteine™ CA is a moisturizer sold by the company SEPPIC.

Schercemol™ OP is an emollient ester with a nongreasy effect.

Lanol™ P is an additive with a stabilizing effect sold by the company SEPPIC.

Parsol™ MCX is octyl para-methoxycinnamate sold by the company Givaudan.

Sepiperl™ N is a pearlescent agent, sold by the company SEPPIC, based on a mixture of alkyl polyglucosides such as those described in WO 95/13863.

Micropearl™ SQL is a mixture of microparticles containing squalane, which is released by the action of massaging; it is sold by the company Matsumo.

Lanol™ 99 is isononyl isononanoate sold by the company SEPPIC.

Lanol™ 37 T is glyceryl triheptanoate sold by the company SEPPIC.

Solagum™ L is a carrageenan sold by the company SEPPIC.

Marcol™ 82 is a liquid paraffin sold by the company Exxon.

Lanol™ 84 D is dioctyl malate sold by the company SEPPIC.

Parsol NOX™ is a sunscreen sold by the company Givaudan.

Eusolex™ 4360 is a sunscreen sold by the company Merck.

Dow Corning™ 245 Fluid is cyclomethicone sold by the company Dow Corning.

Lipacide™ PVB is an acylated wheat protein hydrolyzate sold by the company SEPPIC.

Micropearl™ LM is a mixture of squalane, polymethyl methacrylate and menthol, sold by the company SEPPIC.

Sepicontrol™ A5 is a mixture of capryloyl glycine, sarcosine and extract of Cinnamon zylanicum, sold by the company SEPPIC, such as those described in international patent application PCT/FR98/01313 filed on 23 Jun. 1998.

Lanol™ 2681 is a mixture of coconut caprylate/caprate sold by the company SEPPIC.

Montanov™ 202 is an APG/fatty alcohol composition as described in WO 998/47610, sold by the company SEPPIC.

Easynov™ (INCI name: octyldodecanol, octyldodecyl xyloside and PEG-30 dipolyhydroxystearate) is an emulsifying composition sold by the company SEPPIC.

Aquaxyl™ (INCI name: Xylitylglucoside & Anhydroxylitol & Xylitol) is a moisturizer sold by the company SEPPIC.

Lipacide™ UG (INCI name: undecylenoyl glycine) is a deodorant and dermo-purifying agent sold by the company SEPPIC.

The invention claimed is:

1. A composition in the form of a self-reversible reverse latex comprising, per 100% of its mass:
   a) from 25 mass % to 80 mass % of a crosslinked anionic polyelectrolyte (P), derived from the polymerization, per 100 mol %:
      i) of a molar proportion of greater than or equal to 30% and less than or equal to 95% of monomer units derived from at least one monomer comprising a free or partially or totally salified strong acid function;
      ii) optionally of a molar proportion of greater than or equal to 10% and less than or equal to 65% of monomer units derived from at least one neutral monomer;
      iii) optionally of a molar proportion of greater than or equal to 5% and less than or equal to 65% of monomer units derived from at least one monomer comprising a free or partially or totally salified weak acid function; and
      iv) of a molar proportion of greater than 0% and less than or equal to 5% of at least one diethylenic or polyethylenic crosslinking monomer;
   b) from 0.5 mass % to 10 mass % of a terpolymer of stearyl methacrylate, of pentacosaethoxylated behenyl methacrylate and of N,N-dimethylacrylamide, derived from the polymerization, per 100 mol %, of:
      80 mol % to 95 mol % of stearyl methacrylate, 2.5 mol % to 10 mol % of N,N-dimethylacrylamide and
2.5 mol % to 10 mol % of pentacosaethoxylated behenyl methacrylate,
c) from 5 mass % to 40 mass % of at least one oil, and
d) from 0.1 mass % to 40 mass % of water,
wherein said composition comprises neither oil-in-water surfactants nor water-in-oil surfactants.

2. The composition as defined in claim 1, in which the terpolymer of stearyl methacrylate, of pentacosaethoxylated behenyl methacrylate and of N,N-dimethylacrylamide is selected from the group consisting of:
terpolymer of stearyl methacrylate, of pentacosaethoxylated behenyl methacrylate and of N,N-dimethylacrylamide [(A)/(B)/(C) mol ratio=87/5/8];
terpolymer of stearyl methacrylate, of pentacosaethoxylated behenyl methacrylate and of N,N-dimethylacrylamide [(A)/(B)/(C) mol ratio=80/5/15];
terpolymer of stearyl methacrylate, of pentacosaethoxylated behenyl methacrylate and of N,N-dimethylacrylamide [(A)/(B)/(C) mol ratio=85/10/5];
terpolymer of stearyl methacrylate, of pentacosaethoxylated behenyl methacrylate and of N,N-dimethylacrylamide [(A)/(B)/(C) mol ratio=80/10/10];
terpolymer of stearyl methacrylate, of pentacosaethoxylated behenyl methacrylate and of N,N-dimethylacrylamide [(A)/(B)/(C) mol ratio=90/5/5] and
terpolymer of stearyl methacrylate, of pentacosaethoxylated behenyl methacrylate and of N,N-dimethylacrylamide [(A)/(B)/(C) mol ratio=95/2.5/2.5)].

3. The composition as defined in claim 1, for which, in said anionic polyelectrolyte P, the monomer units comprising a strong acid function are derived from 2-methyl-2-[(1-oxo-2-propenyl)amino]-1-propanesulfonic acid partially or totally salified as the sodium salt, as the potassium salt or as the ammonium salt.

4. The composition as defined in claim 1, in which the mass ratio between said terpolymer of stearyl methacrylate, of pentacosaethoxylated behenyl methacrylate and of N,N-dimethylacrylamide and said anionic polyelectrolyte (P) is greater than or equal to 1/100 and less than or equal to 1/5.

5. The composition as defined in claim 1, in the form of a self-reversible reverse latex comprising, per 100% of its mass:
a) from 25 mass % to 50 mass % of a branched or crosslinked anionic polyelectrolyte (P), derived from the polymerization, per 100 mol %:
i) of a molar proportion of greater than or equal to 30% and less than or equal to 95% of monomer units derived from at least one monomer comprising a free or partially or totally salified strong acid function;
ii) of a molar proportion of greater than or equal to 10% and less than or equal to 65% of monomer units derived from at least one neutral monomer;
and
iv) of a molar proportion of greater than 0% and less than or equal to 5% of at least one diethylenic or polyethylenic crosslinking monomer;
b) from 1 mass % to 5 mass % of a terpolymer of stearyl methacrylate, of pentacosaethoxylated behenyl methacrylate and of N,N-dimethylacrylamide, derived from the polymerization, per 100 mol %;
of 80 mol % to 95 mol % of stearyl methacrylate,
of 2.5 mol % to 10 mol % of N,N-dimethylacrylamide, and
of 2.5 mol % to 10 mol % of pentacosaethoxylated behenyl methacrylate,
c) from 10 mass % to 30 mass % of at least one oil, and
d) from 20 mass % to 40 mass % of water.

6. The composition as defined in claim 1, in the form of a self-reversible reverse latex comprising, per 100% of its mass:
a) from 50 mass % to 80 mass % of a branched or crosslinked anionic polyelectrolyte (P), derived from the polymerization, per 100 mol %:
i) of a molar proportion of greater than or equal to 30% and less than or equal to 95% of monomer units derived from at least one monomer comprising a free or partially or totally salified strong acid function;
ii) of a molar proportion of greater than or equal to 10% and less than or equal to 65% of monomer units derived from at least one neutral monomer;
and
iv) of a molar proportion of greater than 0% and less than or equal to 5% of at least one diethylenic or polyethylenic crosslinking monomer;
b) from 1 mass % to 10 mass % of a terpolymer of stearyl methacrylate, of pentacosaethoxylated behenyl methacrylate and of N,N-dimethylacrylamide, derived from the polymerization, per 100 mol:
of 80 mol % to 95 mol % of stearyl methacrylate,
of 2.5 mol % to 10 mol % of N,N-dimethylacrylamide, and
of 2.5 mol % to 10 mol % of pentacosaethoxylated behenyl methacrylate,
c) from 10 mass % to 40 mass % of at least one oil, and
d) not more than 5 mass % of water.

7. A process for preparing the composition in the form of a self-reversible reverse latex according to claim 1, that comprising:
I) providing aqueous phase (A) comprising said monomer i) and said monomer iv), wherein aqueous phase (A) optionally comprises said monomer ii), said monomer iii), hydrophilic additives, and combinations thereof,
II) emulsifying aqueous phase (A) in organic phase (O), wherein organic phase (O) comprises b) said terpolymer of stearyl methacrylate, of pentacosaethoxylated behenyl methacrylate and of N,N-dimethylacrylamide, and c) said at least one oil, wherein organic phase (O) optionally comprises one or more volatile oils, optional hydrophobic additives, and combinations thereof, wherein c) said at least one oil is intended to be present in the final composition
III) initiating a polymerization reaction by introducing into the emulsion formed in II) a free-radical initiator, and the reaction is then left to proceed to form a reaction medium containing a) said crosslinked anionic polyelectrolyte (P), and
IV) optionally concentrating the reaction medium derived from step III) by distillation, until said optional, one or more volatile oils have been completely removed,
wherein said composition comprises neither oil-in-water surfactants nor water-in-oil surfactants.

8. A process for preparing the composition in the form of a self-reversible reverse latex according to claim 1, that comprising:
providing a terpolymer of stearyl methacrylate, of pentacosaethoxylated behenyl methacrylate and of N,N-dimethylacrylamide, derived from the polymerization, per 100 mol %:
of 80 mol % to 95 mol % of stearyl methacrylate,
of 2.5 mol % to 10 mol % of N,N-dimethylacrylamide and
of 2.5 mol % to 10 mol % of pentacosaethoxylated behenyl methacrylate, as stabilizer for a water-in-oil emulsion comprising:
a crosslinked anionic polyelectrolyte (P), derived from the polymerization, per 100 mol %:
i) of a molar proportion of greater than or equal to 30% and less than or equal to 95% of monomer units derived from at least one monomer comprising a free or partially or totally salified strong acid function,
ii) optionally of a molar proportion of greater than or equal to 10% and less than or equal to 65% of monomer units derived from at least one neutral monomer,
iii) optionally of a molar proportion of greater than or equal to 5% and less than or equal to 65% of monomer units derived from at least one monomer comprising a free or partially or totally salified weak acid function, and
iv) of a molar proportion of greater than 0% and less than or equal to 5% of at least one diethylenic or polyethylenic crosslinking monomer,
at least one oil, and
water; and
carrying out a reverse emulsion polymerization reaction on the water-in-oil emulsion,
wherein said composition comprises neither oil-in-water surfactants nor water-in-oil surfactants.

9. A cosmetic, dermopharmaceutical or pharmaceutical topical composition, comprising, as thickener and/or emulsifier, an effective amount of the composition as defined in claim 1.

10. A method for thickening a cosmetic, dermopharmaceutical or pharmaceutical topical composition comprising at least one aqueous phase, wherein the method comprises adding an effective amount of the self-reversible reverse latex composition of claim 1 to a topical composition comprising at least one aqueous phase.

11. The composition as defined in claim 2, for which, in said anionic polyelectrolyte P, the monomer units comprising a strong acid function are derived from 2-methyl-2-[(1-oxo-2-propenyl)amino]-1-propanesulfonic acid partially or totally salified as the sodium salt, as the potassium salt or as the ammonium salt.

12. The composition as defined in claim 2, in which the mass ratio between said terpolymer of stearyl methacrylate, of pentacosaethoxylated behenyl methacrylate and of N,N-dimethylacrylamide and said anionic polyelectrolyte (P) is greater than or equal to 1/100 and less than or equal to 1/5.

13. The composition as defined in claim 3, in which the mass ratio between said terpolymer of stearyl methacrylate, of pentacosaethoxylated behenyl methacrylate and of N,N-dimethylacrylamide and said anionic polyelectrolyte (P) is greater than or equal to 1/100 and less than or equal to 1/5.

14. The composition as defined in claim 2, in the form of a self-reversible reverse latex comprising, per 100% of its mass:
a) from mass % to 50 mass % of a branched or crosslinked anionic polyelectrolyte (P), derived from the polymerization, per 100 mol %:
i) of a molar proportion of greater than or equal to 30% and less than or equal to 95% of monomer units derived from at least one monomer comprising a free or partially or totally salified strong acid function;
ii) of a molar proportion of greater than or equal to 10% and less than or equal to 65% of monomer units derived from at least one neutral monomer;
and
iv) of a molar proportion of greater than 0% and less than or equal to 5% of at least one diethylenic or polyethylenic crosslinking monomer;
b) from 1 mass % to 5 mass % of a terpolymer of stearyl methacrylate, of pentacosaethoxylated behenyl methacrylate and of N,N-dimethylacrylamide, derived from the polymerization, per 100 mol %;
of 80 mol % to 95 mol % of stearyl methacrylate,
of 2.5 mol % to 10 mol % of N,N-dimethylacrylamide, and
of 2.5 mol % to 10 mol % of pentacosaethoxylated behenyl methacrylate,
c) from 10 mass % to 30 mass % of at least one oil, and
d) from 20 mass % to 40 mass % of water.

15. The composition as defined in claim 3, in the form of a self-reversible reverse latex comprising, per 100% of its mass:
a) from 25 mass % to 50 mass % of a branched or crosslinked anionic polyelectrolyte (P), derived from the polymerization, per 100 mol %:
i) of a molar proportion of greater than or equal to 30% and less than or equal to 95% of monomer units derived from at least one monomer comprising a free or partially or totally salified strong acid function;
ii) of a molar proportion of greater than or equal to 10% and less than or equal to 65% of monomer units derived from at least one neutral monomer;
and
iv) of a molar proportion of greater than 0% and less than or equal to 5% of at least one diethylenic or polyethylenic crosslinking monomer;
b) from 1 mass % to 5 mass % of a terpolymer of stearyl methacrylate, of pentacosaethoxylated behenyl methacrylate and of N,N-dimethylacrylamide, derived from the polymerization, per 100 mol %;
of 80 mol % to 95 mol % of stearyl methacrylate,
of 2.5 mol % to 10 mol % of N,N-dimethylacrylamide, and
of 2.5 mol % to 10 mol % of pentacosaethoxylated behenyl methacrylate,
c) from 10 mass % to 30 mass % of at least one oil, and
d) from 20 mass % to 40 mass % of water.

16. The composition as defined in claim 4, in the form of a self-reversible reverse latex comprising, per 100% of its mass:
a) from 25 mass % to 50 mass % of a branched or crosslinked anionic polyelectrolyte (P), derived from the polymerization, per 100 mol %:
i) of a molar proportion of greater than or equal to 30% and less than or equal to 95% of monomer units derived from at least one monomer comprising a free or partially or totally salified strong acid function;
ii) of a molar proportion of greater than or equal to 10% and less than or equal to 65% of monomer units derived from at least one neutral monomer;
and
iv) of a molar proportion of greater than 0% and less than or equal to 5% of at least one diethylenic or polyethylenic crosslinking monomer;
b) from 1 mass % to 5 mass % of a terpolymer of stearyl methacrylate, of pentacosaethoxylated behenyl methacrylate and of N,N-dimethylacrylamide, derived from the polymerization, per 100 mol;
of 80 mol % to 95 mol % of stearyl methacrylate,
of 2.5 mol % to 10 mol % of N,N-dimethylacrylamide, and
of 2.5 mol % to 10 mol % of pentacosaethoxylated behenyl methacrylate,
c) from 10 mass % to 30 mass % of at least one oil, and
d) from 20 mass % to 40 mass % of water.

17. The composition as defined in claim 2, in the form of a self-reversible reverse latex comprising, per 100% of its mass:
   a) from 50 mass % to 80 mass % of a branched or crosslinked anionic polyelectrolyte (P), derived from the polymerization, per 100 mol %:
      i) of a molar proportion of greater than or equal to 30% and less than or equal to 95% of monomer units derived from at least one monomer comprising a free or partially or totally salified strong acid function;
      ii) of a molar proportion of greater than or equal to 10% and less than or equal to 65% of monomer units derived from at least one neutral monomer;
      and
      iv) of a molar proportion of greater than 0% and less than or equal to 5% of at least one diethylenic or polyethylenic crosslinking monomer;
   b) from 1 mass % to 10 mass % of a terpolymer of stearyl methacrylate, of pentacosaethoxylated behenyl methacrylate and of N,N-dimethylacrylamide, derived from the polymerization, per 100 mol %:
      of 80 mol % to 95 mol % of stearyl methacrylate,
      of 2.5 mol % to 10 mol % of N,N-dimethylacrylamide, and
      of 2.5 mol % to 10 mol % of pentacosaethoxylated behenyl methacrylate,
   c) from 10 mass % to 40 mass % of at least one oil, and
   d) not more than 5 mass % of water.

18. The composition as defined in claim 3, in the form of a self-reversible reverse latex comprising, per 100% of its mass:
   a) from 50 mass % to 80 mass % of a branched or crosslinked anionic polyelectrolyte (P), derived from the polymerization, per 100 mol %:
      i) of a molar proportion of greater than or equal to 30% and less than or equal to 95% of monomer units derived from at least one monomer comprising a free or partially or totally salified strong acid function;
      ii) of a molar proportion of greater than or equal to 10% and less than or equal to 65% of monomer units derived from at least one neutral monomer;
      and
      iv) of a molar proportion of greater than 0% and less than or equal to 5% of at least one diethylenic or polyethylenic crosslinking monomer;
   b) from 1 mass % to 10 mass % of a terpolymer of stearyl methacrylate, of pentacosaethoxylated behenyl methacrylate and of N,N-dimethylacrylamide, derived from the polymerization, per 100 mol %:
      of 80 mol % to 95 mol % of stearyl methacrylate,
      of 2.5 mol % to 10 mol % of N,N-dimethylacrylamide, and
      of 2.5 mol % to 10 mol % of pentacosaethoxylated behenyl methacrylate,
   c) from 10 mass % to 40 mass % of at least one oil, and
   d) not more than 5 mass % of water.

19. The composition as defined in claim 4, in the form of a self-reversible reverse latex comprising, per 100% of its mass:
   a) from 50 mass % to 80 mass % of a branched or crosslinked anionic polyelectrolyte (P), derived from the polymerization, per 100 mol %:
      i) of a molar proportion of greater than or equal to 30% and less than or equal to 95% of monomer units derived from at least one monomer comprising a free or partially or totally salified strong acid function;
      ii) of a molar proportion of greater than or equal to 10% and less than or equal to 65% of monomer units derived from at least one neutral monomer;
      and
      iv) of a molar proportion of greater than 0% and less than or equal to 5% of at least one diethylenic or polyethylenic crosslinking monomer;
   b) from 1 mass % to 10 mass % of a terpolymer of stearyl methacrylate, of pentacosaethoxylated behenyl methacrylate and of N,N-dimethylacrylamide, derived from the polymerization, per 100 mol %:
      of 80 mol % to 95 mol % of stearyl methacrylate,
      of 2.5 mol % to 10 mol % of N,N-dimethylacrylamide, and
      of 2.5 mol % to 10 mol % of pentacosaethoxylated behenyl methacrylate,
   c) from 10 mass % to 40 mass % of at least one oil, and
   d) not more than 5 mass % of water.

20. A cosmetic, dermopharmaceutical or pharmaceutical topical composition, comprising, as thickener and/or emulsifier, an effective amount of the composition as defined in claim 2.

* * * * *